United States Patent
Russhard et al.

(10) Patent No.: US 10,168,306 B2
(45) Date of Patent: Jan. 1, 2019

(54) TIME REFERENCE DERIVATION FROM TIME OF ARRIVAL MEASUREMENTS

(71) Applicant: ROLLS-ROYCE PLC, London (GB)

(72) Inventors: Peter Russhard, Nottingham (GB); Jason David Back, Derby (GB)

(73) Assignee: ROLLS-ROYCE plc, London (GB)

( * ) Notice: Subject to any disclaimer, the term of this patent is extended or adjusted under 35 U.S.C. 154(b) by 781 days.

(21) Appl. No.: 14/601,673

(22) Filed: Jan. 21, 2015

(65) Prior Publication Data

US 2015/0226709 A1 Aug. 13, 2015

(30) Foreign Application Priority Data

Feb. 12, 2014 (GB) .................................. 1402419.4

(51) Int. Cl.
*G01N 29/44* (2006.01)
*G01M 15/14* (2006.01)
(Continued)

(52) U.S. Cl.
CPC ............. *G01N 29/44* (2013.01); *F01D 17/06* (2013.01); *F01D 21/003* (2013.01);
(Continued)

(58) Field of Classification Search
CPC .. G01N 29/07; G01N 29/44; G01N 2291/011; G01N 2291/023; G01N 2291/025; G01M 15/14; F01D 17/06; F01D 21/003; F01D 2270/334; F05D 2260/80; F05D 2270/821; G01H 1/006; G01P 3/489; Y02T 50/671
(Continued)

(56) References Cited

U.S. PATENT DOCUMENTS 4,158,305 A 6/1979 Shipley
4,790,189 A 12/1988 Twerdochlib
(Continued)

FOREIGN PATENT DOCUMENTS

EP 2 136 189 A2 12/2009
EP 2261614 A1 12/2010
(Continued)

OTHER PUBLICATIONS

Aug. 17, 2015 Search Report issued in European Patent Application No. 15 15 175.
(Continued)

*Primary Examiner* — Gregory J Toatley, Jr.
*Assistant Examiner* — Lynda Dinh
(74) *Attorney, Agent, or Firm* — Oliff PLC

(57) ABSTRACT

A rotor arrangement and method by which a time reference is provided for a rotor. The rotor includes N time of arrival features. The method includes steps to: provide a plurality of time of arrival probes spaced apart circumferentially outside the periphery of the rotor; for each revolution of the rotor, measure a time of arrival of each feature at each probe; select N time of arrival measurements at each probe; derive a best fit of the measured times of arrival measured at all the probes against angular position; and set the time reference for the next revolution of the rotor equal to the best fit at the end of the current revolution of the rotor.

19 Claims, 6 Drawing Sheets

(51) Int. Cl.
  *F01D 21/00* (2006.01)
  *G01N 29/07* (2006.01)
  *F01D 17/06* (2006.01)
  *G01P 3/489* (2006.01)
  *G01H 1/00* (2006.01)

(52) U.S. Cl.
  CPC ............ *G01M 15/14* (2013.01); *G01N 29/07* (2013.01); *G01P 3/489* (2013.01); *F05D 2260/80* (2013.01); *F05D 2270/334* (2013.01); *F05D 2270/821* (2013.01); *G01H 1/006* (2013.01); *G01N 2291/011* (2013.01); *G01N 2291/023* (2013.01); *G01N 2291/025* (2013.01); *Y02T 50/671* (2013.01)

(58) Field of Classification Search
  USPC .................................................. 702/179, 56
  See application file for complete search history.

(56) References Cited

U.S. PATENT DOCUMENTS 5,206,816 A    4/1993  Hill et al.
2009/0078052 A1    3/2009  Twerdochlib
2012/0312099 A1*  12/2012  Russhard ................ F01D 17/02
                                            73/660
2013/0304418 A1*  11/2013  Gendrich ................ F01D 17/02
                                            702/182

FOREIGN PATENT DOCUMENTS

EP    2 532 839 A2    12/2012
GB    2 416 848 A     2/2006

OTHER PUBLICATIONS

Zieliski M et al. "Noncontact Vibration Measurements on Compressor Rotor Blades; Rotor Blade Vibration Measurements." vol. 11, pp. 847-856, Jul. 1, 2000.

May 29, 2014 Search Report issued in British Patent Application No. 1402419.4.

* cited by examiner

TIME REFERENCE DERIVATION FROM TIME OF ARRIVAL MEASUREMENTS

BACKGROUND

The present invention relates to deriving a time reference from time of arrival measurements to enable vibration events to be identified and analysed. It finds particular, but not exclusive, utility in deriving a time reference from time of arrival measurements derived from a gas turbine engine rotor, such as from blade tips of such a rotor.

Blade tip displacement data, derived from time of arrival measurements, is analysed to identify vibration events and trends. In order to correctly identify whether vibration is synchronous, that is it occurs at a multiple of the angular speed of rotation of the rotor to which the blades are mounted, or asynchronous, that is it occurs at a non-integer multiple of the angular speed of rotation, it is necessary to have an accurate time reference. Conventionally this time reference is provided once per revolution of the rotor and is known as a once per revolution (OPR) signal. The OPR signal is conventionally provided by a special feature on the rotor which produces a time of arrival measurement that differs from that produced by other features, for example having a different magnitude. Vibrations and other events and trends noted in the time of arrival measurement data can then be compared to each other by their position relative to the OPR signal.

SUMMARY

One problem with using an OPR signal is that a special OPR probe is required to detect the OPR feature on the rotor. For a gas turbine engine rotor application the OPR probe is generally mounted so that it is close to the rotor hub and to the engine centreline, for example in a front bearing chamber. It is necessary to modify the rotor to provide the feature monitored by the OPR probe. However, this means it is exposed to high temperature and is positioned in a restricted space which increases its probability of failure, temporary or permanent, and increases its cost.

Another problem with using an OPR signal is that the OPR probe is a comparatively heavy and bulky component. Thus there is a weight penalty associated with providing an OPR probe and particularly for providing two OPR probes, as is beneficial for redundancy. There is also a consequential performance penalty caused by the size of the OPR probe or probes moving or resizing other components in the gas turbine engine away from their otherwise optimal positions or sizes. A further problem is that the spatial resolution that can be achieved by suitable OPR probes is lower than that achievable by the blade tip timing probes and the OPR probe is subject to vibration itself. Thus the accuracy of blade tip timing measurements is limited by the resolution and accuracy of the OPR probe.

The present invention provides a method of providing a time reference and a rotor arrangement that seeks to address the aforementioned problems.

Accordingly the present invention provides a method of providing a time reference for a rotor, the rotor comprising N time of arrival features; the method comprising steps for each revolution of the rotor to:
a) provide a plurality of time of arrival probes spaced apart circumferentially outside the periphery of the rotor;
b) measure a time of arrival of each feature at each probe;
c) select N time of arrival measurements at each probe, wherein the first time of arrival measurement selected at each probe is greater than or equal to a time reference;
d) derive a best fit of the measured times of arrival measured at all the probes against angular position; and
e) set the time reference for the next revolution of the rotor equal to the best fit at the end of the current revolution of the rotor.

Advantageously the method provides a time reference which can replace an OPR signal and therefore result in the removal of an OPR probe. Consequently the present invention results in weight reduction of the rotor assembly to which the method is applied. Advantageously the method provides a more accurate time reference than previous methods without the noise introduced from an OPR probe. Advantageously the method may provide more than one time reference, for example corresponding to positions around the rotor where vibration effects are expected due to components outside the rotor.

Advantageously the method is robust because measurements may be taken from lots of probes but the time reference may be generated even if data from some of the probes has to be discarded as 'bad'. It is also robust because measurements from probes that have experienced 'bad' data can be used again in subsequent revolutions of the rotor.

The initial time reference used in step c) may be chosen as the smallest time of arrival measurement measured at all the probes. Alternatively it may be chosen as equal to the expected time for one revolution of the rotor or a fixed value such as zero. Advantageously the initial time reference need not be an accurate estimate for the method to succeed. Advantageously the initial time reference is replaced by the calculated time reference in subsequent revolutions of the rotor.

Advantageously the method may be applied in real-time, using measurements taken as the method is run. Thus the method can be used as an input to a control algorithm for the rotor. It can also be used to indicate when future repair or maintenance of the rotor is advisable. Alternatively the method may be applied 'off-line' to measurements collected previously. Thus the method may be used to reanalyse historical data with more accuracy than was available when the measurements were taken.

The method may comprise further steps after step c) to:
c1) for times of arrival measured at each probe:
i) derive a best fit of the measured times of arrival against angular position;
ii) calculate a difference between the measured times of arrival and the best fit times of arrival;
iii) calculate standard deviation of the differences; and
iv) discard N time of arrival measurements where the standard deviation is greater than a threshold.

Advantageously the further steps enable discarding data from probes having one or more measurement corresponding to one or more features passing the probe either missing or registered twice for a particular revolution. Step ii) (calculating the difference) may comprise subtracting the measured times of arrival from the best fit times of arrival or vice versa. The threshold used in step iv) may be calculated by steps to:
  choose a standard deviation of the differences with an exponent that is equal to the mode of the exponents of all the standard deviations for the current revolution; and
  double it.

Advantageously this applies the six sigma principal to identify probes having measurements with a standard deviation more than twice the average. Advantageously this identifies probes having measurements where the standard deviation is not of the same order of magnitude, within an acceptable margin, as the other standard deviations for that revolution. Alternatively step b) of the threshold calculation may comprise multiplying the selected standard deviation by a different multiple. The standard deviation chosen in step a) of the threshold calculation may be the largest of the standard deviations having the modal exponent (that is, the most common exponent). Alternatively it may be an arbitrary standard deviation having the modal exponent.

The first time of arrival measurement measured at the first probe may be less than or equal to the first time of arrival measurement measured at any of the other probes. Advantageously this orders the measurements. Also advantageously this helps to ensure that the selected N time of arrival measurements for each probe relate to the same revolution of the rotor.

The method may comprise a further step after optional step c1)ii) (calculate the difference) to plot the differences against angular position as a stack plot in time. Advantageously the stack plots can therefore be produced earlier than in previously used methods. Advantageously the stack plots contain less noise because there is little processing of the measurements before plotting.

The method may further comprise a step to identify a missing or additional measured time of arrival measured at a probe. This may be achieved by sub-steps to:

shift each stack plot by a number of angular intervals equal to a number of angular intervals between the probe and the reference time; and perform a cross-correlation of measured times of arrival from pairs of the probes.

Advantageously the number of angular intervals between each probe and the reference time may be determined once and looked up for each use of these sub-steps so the required processing is limited.

The cross-correlation step may comprise performing a cross-correlation of all the measured times of arrival measured at each of the pairs of probes. Advantageously this guarantees to identify probes with missing or additional time of arrival measurements. Alternatively the cross-correlation step may comprise performing a cross-correlation of the measured time of arrival of one feature measured at each of the pairs of probes. Advantageously this is quick and less processor-intensive to identify probes with missing or additional time of arrival measurements, with reasonable accuracy.

The method may comprise a further step to discard all measured times of arrival measured at a probe if the cross-correlation is less than a predetermined threshold. The threshold may be 90%. Alternatively the threshold may be 95%. The threshold may advantageously correspond to confidence levels.

The method may comprise a further step to calculate an inter-revolution difference between the measured times of arrival measured at a probe and the derived best fit of the measured times of arrival measured at all the probes for a previous revolution of the rotor.

Where measurements from a probe have been discarded references to "all the probes" should be read to mean all the remaining probes.

The steps of deriving a best fit may comprise plotting the measured times of arrival and fitting a line thereto. The line may be linear or curvilinear. For example, it may be a straight line with equation $y=mx+c$ or may be a curve having the form of a quadratic, cubic, or higher order polynomial equation; or it may be sinusoidal, logarithmic or exponential in form; or it may be governed by a more complex relationship. Alternatively the steps of deriving a best fit may comprise a computational method. Advantageously when the method is applied to a rotor that rotates at substantially constant speed the best fit is likely to be described by the equation $y=mx+c$. When the method is applied to a rotor that is accelerating or decelerating it is likely to be described by a higher order polynomial. Advantageously the speed of rotation can therefore be derived from the gradient of the best fit line or, equivalently, the first derivative of the equation describing the best fit for that revolution of the rotor. Advantageously there is no need for independent speed monitoring. Therefore there is a beneficial weight reduction in removing any speed probes formerly provided for the rotor.

There is also provided a computer readable medium, having a computer program recorded thereon, wherein the computer program is adapted to make the computer execute the method described above. There is also provided a computer program having instructions adapted to carry out the method according to the description above or comprising the computer readable medium described.

There is provided a rotor arrangement comprising:
a rotor having time of arrival features;
a plurality of time of arrival probes spaced apart circumferentially outside the periphery of the rotor;
a processor adapted to receive time of arrival measurements from each probe and to calculate a time reference therefrom.

Advantageously the rotor arrangement does not require an OPR probe.

The time of arrival features may be on the surface of the rotor or spaced therefrom. The rotor may comprise a shaft or a bladed rotor. Where the rotor is a shaft, the time of arrival features may be on its surface. Where the rotor is a bladed rotor, the time of arrival features may comprise the blades or may comprise features on the tips of the blades.

The probes may be unequally spaced circumferentially but be at equal distance from an axis of rotation of the rotor. Advantageously such probes may therefore also be used to detect vibration of the rotor at a plurality of excitation modes. Alternatively the probes may be equally spaced circumferentially. Advantageously the rotor arrangement may be one where the circumferential spacing is constrained by other components or other reasons; for example, a turbine rotor stage of a gas turbine engine.

The time of arrival features may comprise any one or more of the group comprising: rotor blades; grooves; ridges; and lines that are optically distinguishable from other parts of the rotor. The features may extend axially. Alternatively they may extend axially and circumferentially. The probes may be optical, microwave, radio frequency or any other probes that are suitable for measuring times of arrival as known in the art.

There is also provided a gas turbine engine comprising the rotor arrangement as described. The rotor may comprise one of the group comprising: a fan rotor; a compressor rotor; a turbine rotor; a shaft; a propeller rotor. Alternatively there is provided a wind turbine, tidal turbine or power turbine comprising the rotor arrangement as described. The rotor may comprise a turbine rotor or a shaft. Alternatively there is provided a machine tool, water wheel or turbocharger comprising the rotor arrangement as described. The rotor may comprise a shaft or wheel. Alternatively there is provided a pumping arrangement comprising the rotor arrangement described. The rotor may comprise a shaft or pumping arms.

Any combination of the optional features is encompassed within the scope of the invention except where mutually exclusive.

BRIEF DESCRIPTION OF THE DRAWINGS

The present invention will be more fully described by way of example with reference to the accompanying drawings, in which.

DETAILED DESCRIPTION OF EMBODIMENTS

Figure 1:
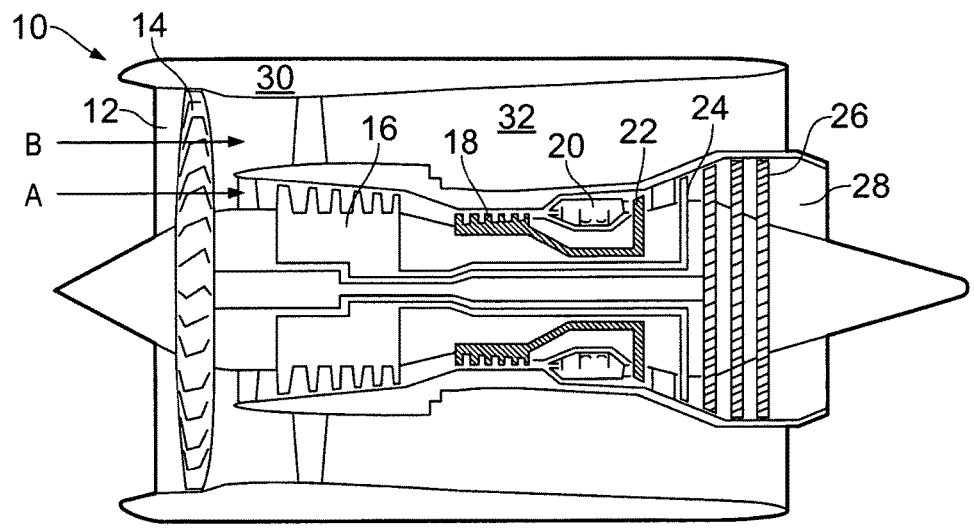
FIG. 1 is a sectional side view of a gas turbine engine.

A gas turbine engine 10 is shown in FIG. 1 and comprises an air intake 12 and a propulsive fan 14 that generates two airflows A and B. The gas turbine engine 10 comprises, in axial flow A, an intermediate pressure compressor 16, a high pressure compressor 18, a combustor 20, a high pressure turbine 22, an intermediate pressure turbine 24, a low pressure turbine 26 and an exhaust nozzle 28. A nacelle 30 surrounds the gas turbine engine 10 and defines, in axial flow B, a bypass duct 32.

Figure 2:
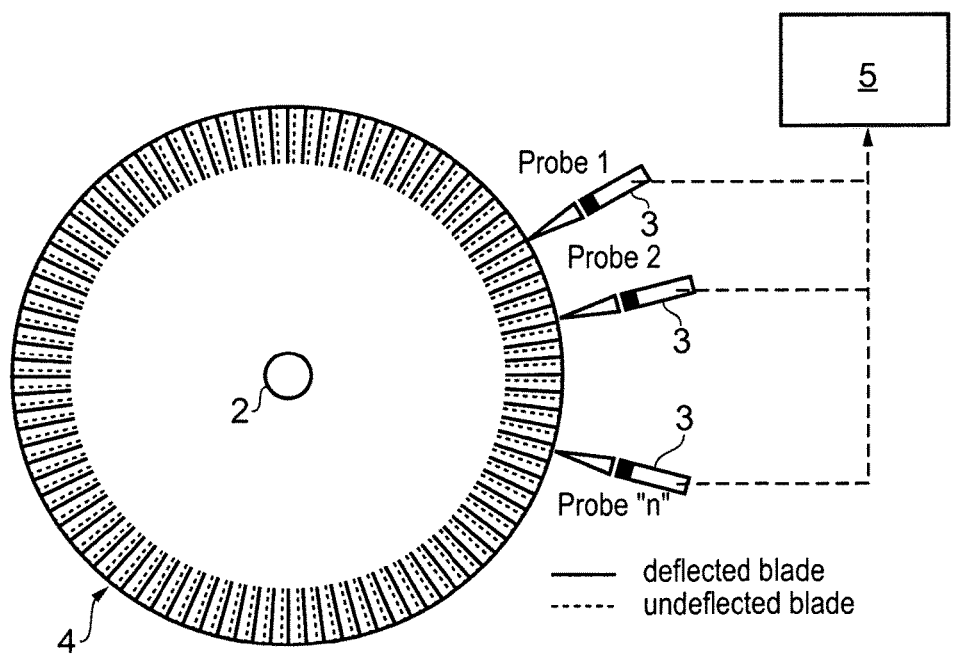
FIG. 2 is a schematic drawing of a blade tip timing arrangement.

FIG. 2 shows schematically a blade tip timing (BTT) arrangement. BTT probes 3 are mounted to a casing (not shown) and provide time of arrival measurements of the blades 4 mounted to the rotor 2. For example, the rotor 2 and blades 4 arrangement may be the fan 14, one of the stages of the intermediate pressure or high pressure compressor 16, 18 or one of the stages of the low pressure, intermediate pressure or high pressure turbine 22, 24, 26. The measurements are passed to a processor 5. The processor 5 may be a dedicated BTT processor. Alternatively it may be a function of or combined with an engine controller, such as the engine electronic controller or full authority digital engine controller (FADEC).

In an embodiment of the present invention there are nine BTT probes 3 provided which are spaced around at least some of the circumference of the casing. Alternatively there may be a different number of probes 3, subject to a minimum of two. The accuracy of the method is improved with more than two BTT probes 3, for example at least four BTT probes 3 may be used in some embodiments. Preferably the probes 3 are irregularly spaced circumferentially so that vibrations at different excitation frequencies are captured. An example set of probes may be located at 353.2°, 326.6°, 319.1°, 295.7°, 285.7°, 271.9°, 264.5°, 237.4° and 207.3°, each measured from top dead centre of the engine 10.

Alternatively the probes 3 may be equally spaced circumferentially about the whole of the casing or a segment thereof. Preferably all the probes 3 are positioned at the same distance radially from the axis of rotation of the rotor 2.

The method of the present invention seeks to derive a time reference from time of arrival measurements recorded by the BTT probes 3 to replace the conventional OPR signal. Advantageously the OPR probe or probes may therefore be omitted, with consequent weight and size benefits. Advantageously more than one time reference may be derived so that a time reference may be close to a feature of interest. For example, where there is a gearbox or other component mounted close to the rotor 2 a time reference may be derived that corresponds to a position close to that component. Little noise is therefore introduced between the time reference and measured times of arrival close to the component so it is simple to analyse whether observed patterns in the times of arrival are correlated to the position of the component, and therefore potentially caused by its proximity, or whether they are uncorrelated, and therefore caused by something else.

Figure 3:
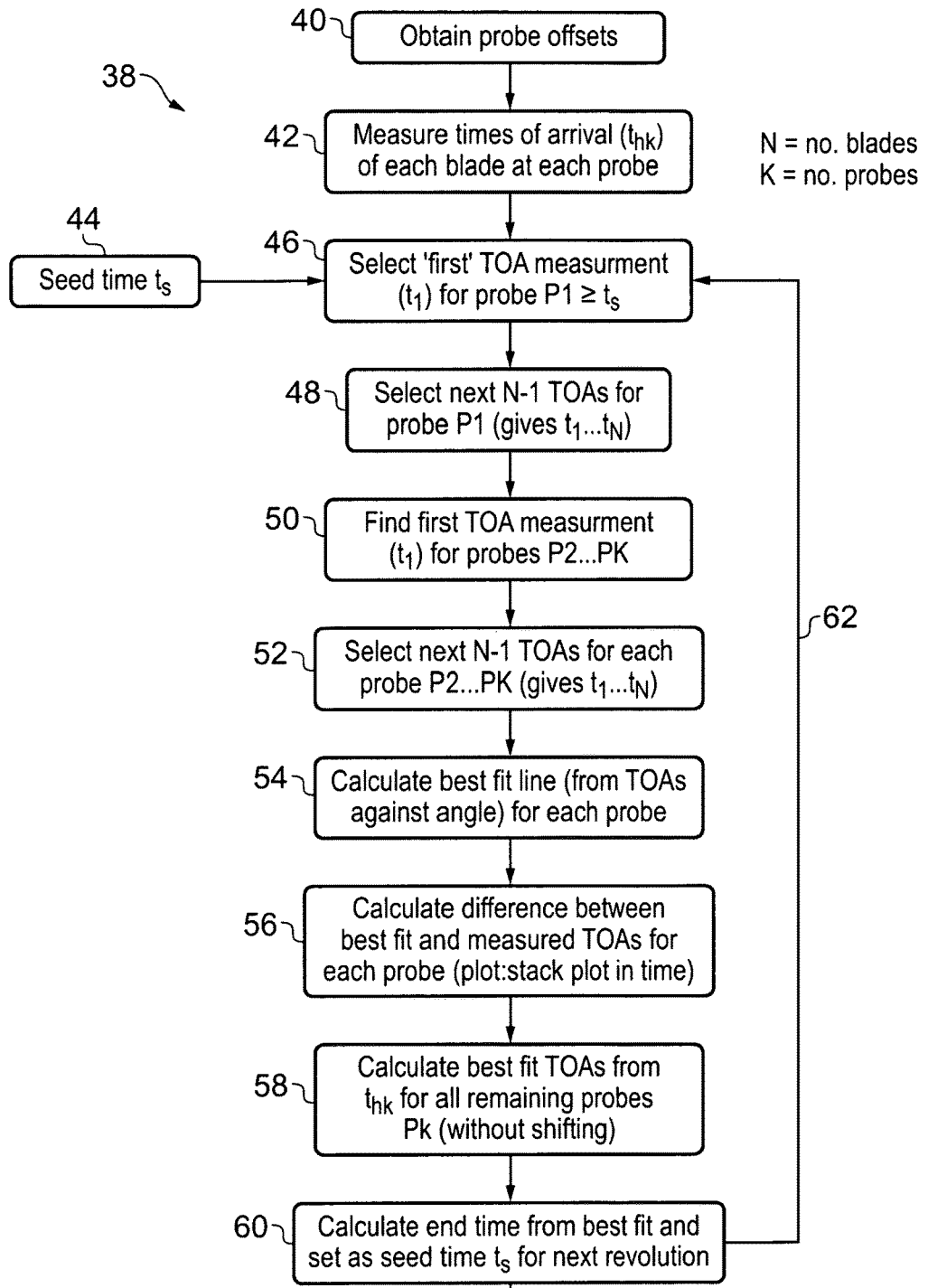
FIG. 3 is a flow chart showing steps of the method according to the present invention.

FIG. 3 is a flow chart of steps of the method 38 according to aspects of the present invention. First the offset of each probe 3 from a defined 0° point, for example top dead centre of the rotor 4, is obtained box 40. The probe offsets are therefore the angular positions of each probe 3. The probe offsets may be obtained by design or by measuring the actual circumferential position of each probe 3 from the 0° point, particularly if the position tolerance compared to design is loose. Each probe 3 is arranged or configured to measure the time of arrival (TOA) of a blade 4 or another feature on the rotor 2. Thus at box 42 the time of arrival $t_{hk}$ of each blade 4 at each probe 3 is measured. The measurements may advantageously be recorded in a matrix having dimensions h×k where h is an index of the measurements and k is the number of probes 3, which may be numbered from $P_1$ to $P_K$. For one revolution of the rotor 2, index h should be equal to the number N of blades 4 (but h=1 does not necessarily correspond with "blade 1" of the set of rotor blades 4).

To initiate the method 38 an initial time reference, seed time $t_s$, is provided—box 44. This initial time reference $t_s$ may be chosen substantially arbitrarily or may be selected on the basis of prior knowledge of the time for one revolution of the rotor 2 or may be selected on the basis of prior knowledge of the early time of arrival measurements of the probes 3.

At box 46 a first time of arrival measurement $t_{11}$ for the first probe $P_1$ is selected from the measured times of arrival $t_{hk}$. The first measurement $t_{11}$ selected is chosen to be greater than or equal to the seed time $t_s$. At box 48 a further N−1 sequential time of arrival measurements $t_{h1}$ for probe $P_1$ are selected from the measurements. Thus N times of arrival $t_{11} \ldots t_{N1}$ are selected, each of which is larger than the previous times in the sequence.

At box 50 a first time of arrival measurement $t_{1k}$ for each of the other probes $P_2$ to $P_K$ are selected from the times of arrival $t_{hk}$ measured at box 42. Each first time of arrival measurement $t_{1k}$ is selected to be greater than or equal to the first measurement $t_{11}$ for probe $P_1$. Preferably each first time of arrival measurement $t_{1k}$ is also selected to be smaller than the second time of arrival measurement $t_{21}$ of probe $P_1$. Beneficially this applies a known ordering to the selected data. However, it is also possible to perform the subsequent steps of method 38 without this ordering. In this case, N sequential time of arrival measurements $t_{1k} \ldots t_{Nk}$ are selected for each probe $P_1 \ldots P_K$.

At box 52 a further N−1 time of arrival measurements $t_{2k} \ldots t_{Nk}$ are selected that sequentially follow the first measurements $t_{1k}$ for each probe $P_2 \ldots P_K$. Thus there are N time of arrival measurements $t_{Nk}$ selected for each probe 3.

At box 54 a best fit is calculated for the selected time of arrival measurements $t_{1k} \ldots t_{Nk}$ for each probe $P_k$. For example, the selected time of arrival measurements $t_{1k} \ldots t_{Nk}$ may be plotted against the blade intervals, adjusted for probe angular offset, and a best fit line be calculated. Alternatively the best fit to the data may be calculated without plotting a graph by known mathematical techniques. When the rotor 2 is rotating at substantially constant angular velocity the best fit line will be a straight line having the form y=mx+c, where m and c are each constants, y is the time of arrival and x is the angle. This is the simplest case and will be used in the ensuing description. However, when the rotor 2 is accelerating or decelerating during the revolution from which the times of arrival $t_{hk}$ were measured, the best fit line will be a non-linear curve. For example, it may be quadratic or higher order polynomial in form or may be logarithmic, exponential, sinusoidal or described by any other mathematical relationship as will be apparent to the skilled reader.

Figure 4:
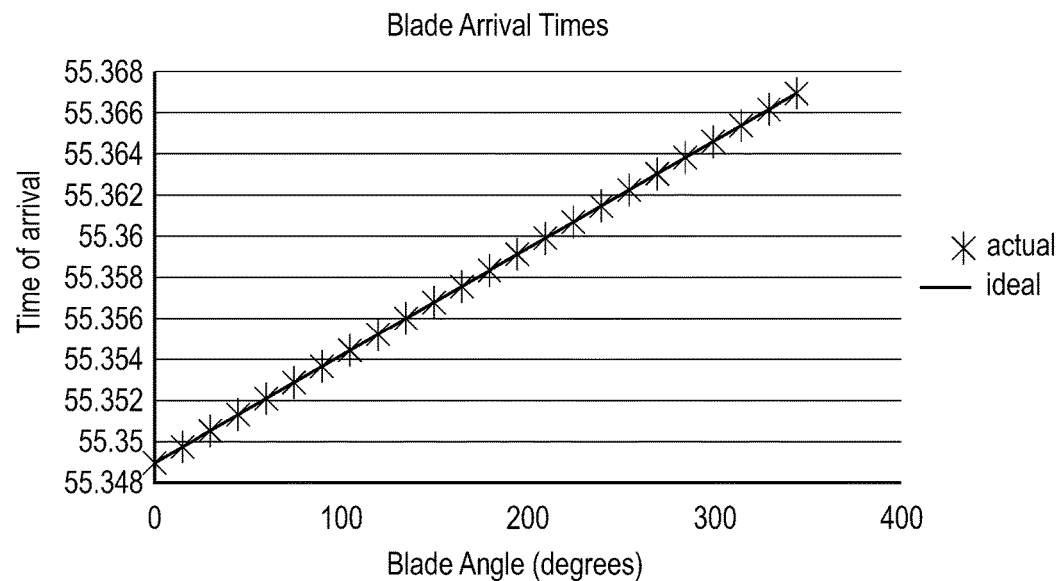
FIG. 4 is a graph of times of arrival.

FIG. 4 shows exemplary measured times of arrival $t_{1k} \ldots t_{Nk}$ for a probe $P_k$. It also shows the derived or calculated best fit line, labelled "ideal". As can be seen in FIG. 4, some of the measured times of arrival $t_{hk}$ lie above the best fit line and others lie below it. The measurements are plotted at intervals corresponding to the angular distance between the blades 4 that are the features from which the time of arrival measurements $t_{hk}$ are taken; as plotted the blade interval is 15° because there are twenty-four blades 4. In the example, either the probe $P_k$ is located at the 0° position or the measurements have been adjusted for the probe offset angle so that the first measurement is plotted at angle 0°.

For measurements from each probe $P_k$ the difference between the best fit times of arrival $t_{BF}$ at each angular interval and the measured times of arrival $t_{hk}$ at the same angular interval can be calculated—box 56. The difference is calculated by subtracting the measured times of arrival $t_{hk}$ from the best fit times of arrival $t_{BF}$, or vice versa. The differences result from vibration and mechanical tolerance variation of the blades 4 from which the times of arrival $t_{hk}$ are measured by the probes $P_k$. Where there is no error in the probe 3 or in the measurements $t_{hk}$ the differences are small, typically of the order of $10^{-6}$. Advantageously these time differences can be plotted against angle as a stack plot in time, to characterise the manufacturing difference in blade spacing. This is in contrast to prior methods in which the stack plots were generated in displacement, against blade number. Advantageously, generating the stack plots in time requires considerably less processing, and so can be outputted earlier in the method 38, and tends to introduce less noise because it requires less processing.

Figure 5:
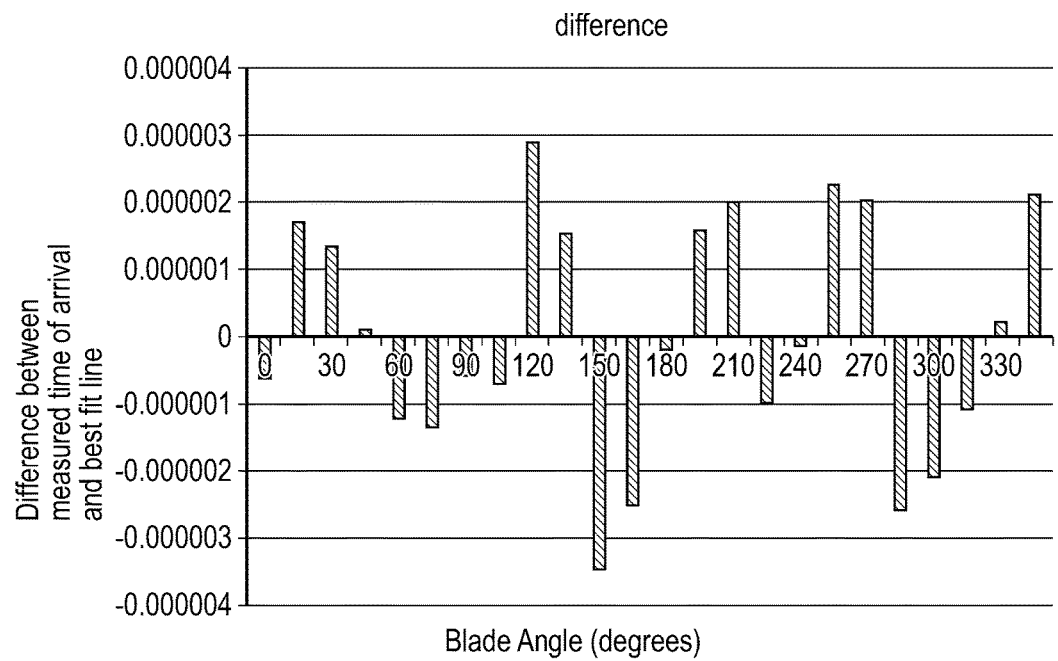
FIG. 5 is a stack plot showing the differences between measured and best fit times of arrival.

FIG. 5 is a stack plot of the differences between the time of arrival measurements $t_{hk}$ and the best fit line shown in FIG. 4. The magnitudes of the differences are all of the order $10^{-6}$ and show a distinct pattern. This pattern will be replicated in the calculated differences for each probe $P_k$ but will be shifted left or right by a number of blade intervals. The number of blade intervals by which a stack plot pattern must be shifted to overlay the pattern from another probe is the integer part of the result of dividing the probe offset by the blade interval. Thus the stack pattern produced at a probe $P_k$ located at probe angle 97.3° must be shifted by six blade intervals relative to the stack pattern produced by the same rotor 2 at a probe $P_k$ located at probe angle 0° where the blade interval is 15°.

The steps described with respect to boxes 54 and 56 are, however, optional steps which may be omitted in some embodiments.

At box 58 another best fit line is calculated. However, at this step of the method 38 all of the selected time of arrival measurements $t_{11} \ldots t_{NK}$ are used. As for the best fit per probe 3 in box 54, the time of arrival measurements $t_{hk}$ may be plotted against angle and the best fit found graphically or the best fit may be found mathematically. Also as for the best fit per probe 3 calculated in box 54, when the rotor 2 is rotating at substantially constant angular velocity the best fit line will be a straight line having the form y=mx+c, where m and c are each constants, y is the time of arrival and x is the angle. This is the simplest case and will be used in the ensuing description. However, when the rotor 2 is accelerating or decelerating during the revolution from which the times of arrival $t_{hk}$ were measured, the best fit line will be a non-linear curve. For example, it may be quadratic or higher order polynomial in form or may be logarithmic, exponential, sinusoidal or described by any other mathematical relationship as will be apparent to the skilled reader.

Due to the circumferential spacing of the blades 4, or other time of arrival features, and the circumferential spacing of the probes $P_k$ the first selected time of arrival measurement $t_{1k}$ at each probe $P_k$ is not the time of arrival of the same blade 4. This has the effect of partially randomising or scattering measurement errors and vibrations across the time of arrival measurement data and therefore reducing the cumulative error or noise. Hence the best fit time of arrival line determined from the measurements at all the probes $P_k$ is a better fit to the measurements than is the case for individual probes $P_k$.

For the simplest case in which the best fit line is a straight line it is trivial to derive the best fit time of arrival $t_{BF}$ at the end of the revolution, where the angle is 360°. It is also possible to determine the best fit time of arrival $t_{BF}$ at the end of the revolution, where the angle is 360°, for an accelerating or decelerating rotor 2. At box 60 the best fit time of arrival $t_{BF}$ at the end of the revolution is determined and is set as the seed time $t_s$ for the next revolution of the rotor 2. The best fit time of arrival $t_{BF}$ at a different point in the revolution may also be determined and used as a time reference point, for example to test a theory that the cause of synchronous vibration is a component at a particular position outside but close to the rotor. Advantageously the seed time $t_s$ and any other determined best fit time of arrival $t_{BF}$ are 'stable' time references because they can be determined at the same angular position for each revolution of the rotor 2. Thus they act effectively as one or more OPR signal without imposing a requirement for an OPR probe.

Iteration branch 62 feeds the calculated seed time $t_s$ back to box 46 to enable the method 38 to iterate for the next revolution of the rotor 2. Thus in the second and subsequent iterations of the method 38 the first time of arrival measurement $t_{11}$ selected at step 46 from the measurements taken at probe $P_1$ is equal to or greater than the seed time $t_s$ calculated at box 60 in the previous iteration of the method 38 instead of the initial seed time $t_s$ from box 44.

Figure 6:
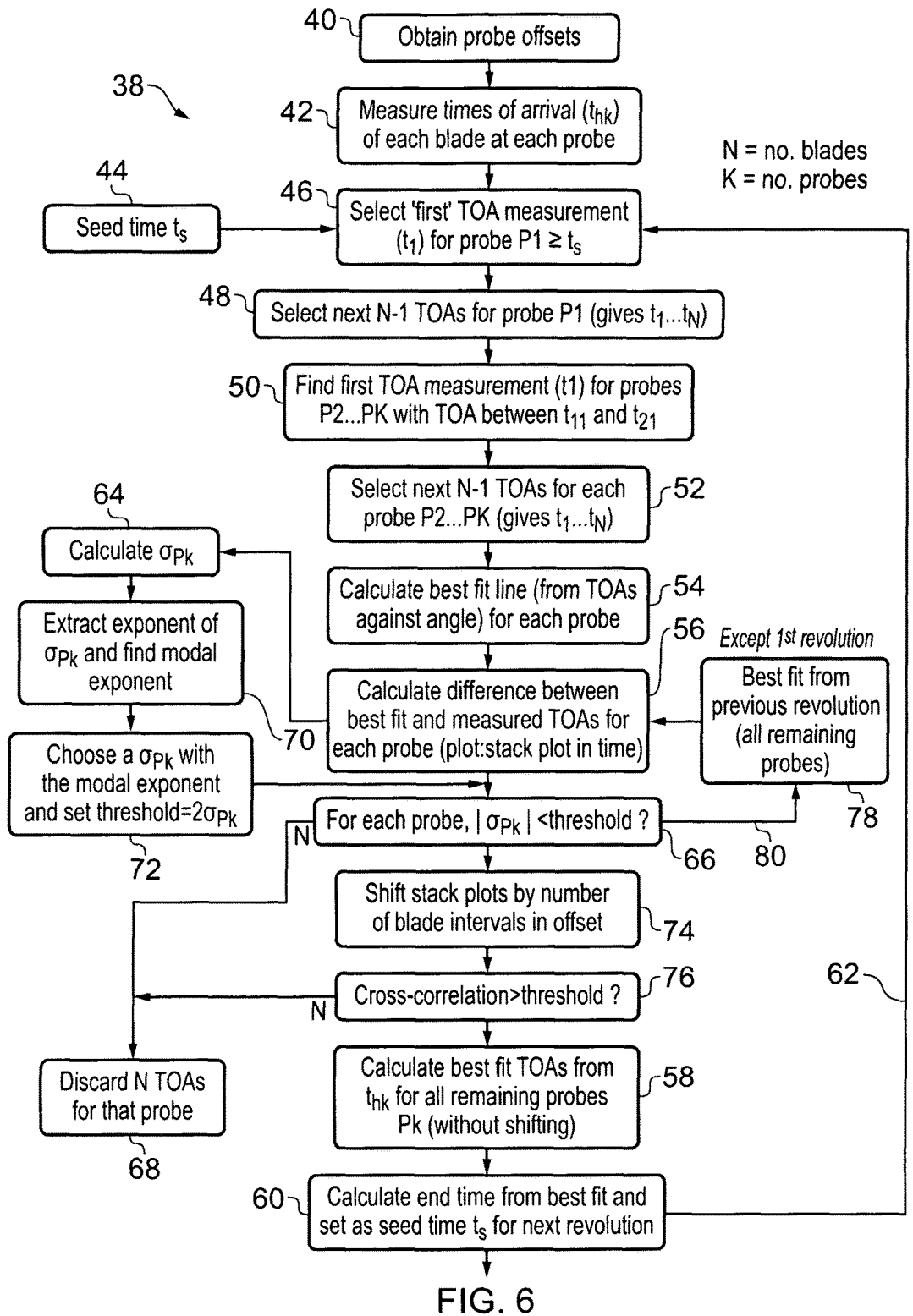
FIG. 6 is a flow chart showing additional optional steps of the method according to the present invention.

FIG. 6 is similar to FIG. 3 and includes all the steps shown in that figure. However, it also includes additional steps of the method 38 which are optional.

Optionally after calculating the difference between the time of arrival measurements $t_{hk}$ and the best fit per probe $P_k$ at box 56, the method 38 may include a step to calculate the standard deviation $\sigma_{Pk}$ of the differences for the measurements from each probe $P_k$—box 64. At box 66 the standard deviation $\sigma_{Pk}$ of the differences is compared to a threshold. If the standard deviation $\sigma_{Pk}$ does not exceed the threshold the time of arrival measurements $t_{hk}$ from that probe $P_k$ for that revolution are retained and the method 38 continues with calculating the best fit times of arrival $t_{BF}$ for the measurements from all the probes $P_k$ (step 58). However, if the standard deviation $\sigma_{Pk}$ of the differences exceeds the threshold at box 66, the selected N times of arrival $t_{1k} \ldots t_{Nk}$ from that probe $P_k$, corresponding to that revolution, are discarded—box 68.

This means that the time of arrival measurements $t_{hk}$ from that probe $P_k$ are not used in the best fit calculation at box 58. If none of the standard deviations $\sigma_{Pk}$ of the differences from any of the probes $P_k$ pass the test in box 66 all the time of arrival measurements $t_{hk}$ for that revolution of the rotor 2 are discarded at box 68 and the method 38 is restarted for the following revolution. Either a new initiating seed time $t_s$ may be estimated at box 44 or a seed time $t_s$ may be calculated at box 60 of the previous good iteration of the method 38 in which there was at least one probe $P_k$ with 'good' measurements $t_{hk}$ (that is, the test in box 66 was passed) by setting the angle for the end time to be 720° instead of 360°.

One optional method of setting the threshold used in box 66 is to dynamically analyse the set of standard deviations $\sigma_{Pk}$ of the differences for all the probes $P_k$ for that revolution of the rotor 2. For example, at box 70 extract the exponent of each standard deviation $\sigma_{Pk}$ and find the most frequently occurring number, the mode. Thus where all the probes $P_k$ have measured 'good' times of arrival $t_{hk}$, the differences will all be of the order of $10^{-6}$ and so the modal exponent will be six. This will also be the case where a minority of the probes $P_k$ have 'bad' measurements $t_{hk}$.

Optionally at box 72 one of the standard deviations $\sigma_{Pk}$ which has the modal exponent is selected. For example, an arbitrary one or the largest of the standard deviations $\sigma_{Pk}$ with the modal exponent may be selected. The threshold is then set to be twice the selected standard deviation $\sigma_{Pk}$; this corresponds to ~99% confidence. Another multiple can be used instead. This optional method of setting the threshold is predicated on the knowledge that where 'bad' time of arrival measurements $t_{hk}$ are produced at a probe $P_k$ for a revolution of the rotor 2 it changes the standard deviation $\sigma_{Pk}$ by approximately two orders of magnitude, for example to the order of $10^{-4}$, and so a coarsely generated threshold will be adequate to distinguish probes $P_k$ for which the time of arrival measurements $t_{hk}$ should be discarded at box 68 for that revolution.

One alternative to the threshold generation method described with respect to boxes 70 and 72 is to set a static absolute threshold. Thus a predetermined threshold value can be chosen and used for multiple iterations of the method 38 without reference to the measurements made at each probe $P_k$ at box 42. Alternatively a predetermined but varying threshold may be set that follows a predetermined trajectory during iterations of the method 38.

A further optional step of the method 38 is shown in box 74. This step, when used, may occur after the optional steps in boxes 64, 70, 72 and 66, or may occur simultaneously with those steps, or may occur instead of those steps. As discussed above the stack plot generated from the time of arrival measurements $t_{hk}$ made at one probe $P_k$ exhibits the same pattern but shifted left or right relative to the stack plot generated from the time of arrival measurements $t_{hk}$ made at another of the probes $P_k$. In box 74 each stack plot is shifted by the calculated number of blade intervals as discussed with respect to FIG. 5. By shifting the stack plots in this manner the calculated differences for the time of arrival measurements $t_{hk}$ made at each probe $P_k$ are adjusted to relate to the same blade 4 at the same position on the x-axis.

Figure 7:
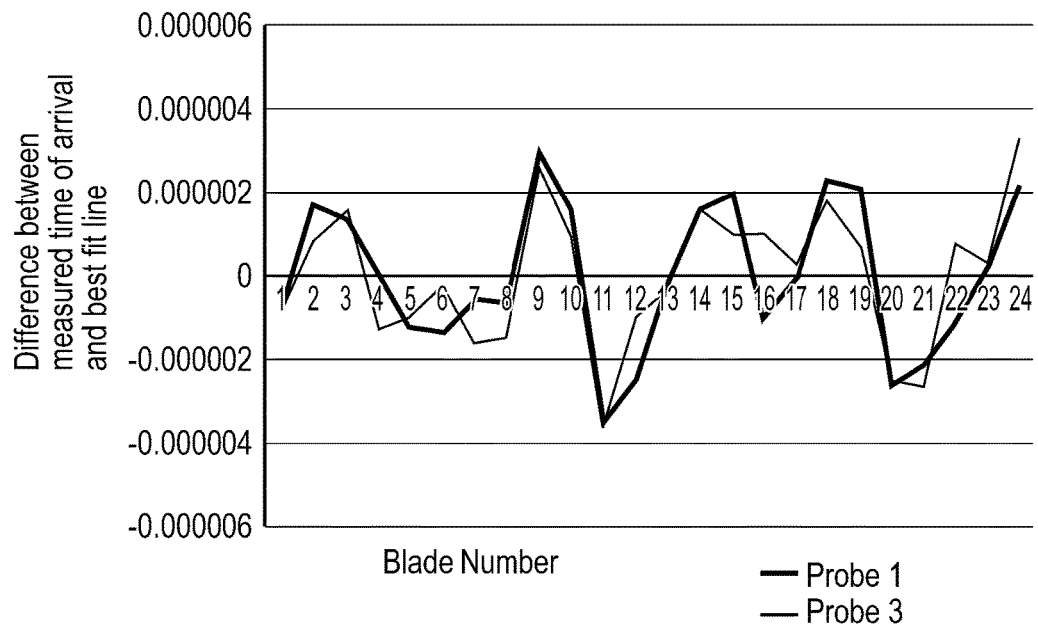
FIG. 7 is a graph showing two stack plots derived from two probes.

FIG. 7 shows a pair of stack plots derived from two probes $P_1$ and $P_3$ of a set of K probes $P_k$. The stack plots are plotted against the blade numbers, where "blade 1" is assigned arbitrarily from amongst the blades 4. As can be seen in the figure both stack plots have the same pattern of positive and negative points, and the magnitude at each blade number is also broadly similar. The amount of similarity between any pair of stack plots derived from the probes $P_k$ can be used as an indication of whether there are any 'bad' time of arrival measurements $t_{hk}$ in the measurements made at any of the probes $P_k$ during that revolution of the rotor 2. One way in which to analyse the similarity between stack plots is by performing a cross-correlation, for example using the Pearson correlation calculation.

In box 76 of FIG. 6 a cross-correlation of the differences from pairs of stack plots is performed and compared to a threshold. There are two alternative methods of performing the cross-correlation of the differences. Firstly, a complete cross-correlation of all the differences for each pair of probes $P_k$ may be performed. This method gives an accurate cross-correlation but is processor intensive for even modest N, for example of the size expected for blade tip timing of a gas turbine engine rotor 2. The second method comprises cross-correlating only the difference of the time of arrival measurement $t_{hk}$ of one blade 4 for each of a pair of the probes $P_k$. This method is faster than the first method, because far fewer points are used, but presupposes that any errors will manifest in the blade 4 chosen and not in a different one of the set of blades 4.

The result of the cross-correlation, howsoever performed, is then compared to a predefined threshold. The threshold may be, for example, 90%. Alternatively it may be set to a higher value, for example to 95%. Where the result of the cross-correlation exceeds the threshold the time of arrival measurements $t_{hk}$ from that probe $P_k$ for that revolution of the rotor 2 are used in the subsequent steps of the method, box 58 onwards. In this case the time of arrival measurements $t_{hk}$ are used as selected and not as shifted at box 74. However, where the result of the cross-correlation does not exceed the threshold, the N time of arrival measurements $t_{hk}$ from that probe $P_k$ relating to that revolution of the rotor 2 are discarded at box 68 of the method 38. The cross-correlation is less than the threshold when the probe $P_k$ has measured an additional or has missed a time of arrival measurement $t_{hk}$, typically because the vibration of the blade 4 has coincided with it passing the angular position of the probe $P_k$ or because of limitations in the probe $P_k$ or acquisition system.

If the comparison of the cross-correlations with the threshold results in discarding the time of arrival measurements $t_{hk}$ from all the probes $P_k$ for that revolution of the rotor 2, the method 38 is restarted for the next revolution using a new seed time $t_s$, either estimated at box 44 or calculated from an earlier iteration in box 60.

Preferably for the second and subsequent iterations of the method 38 the optional loop comprising boxes 64 and 66 is performed twice. First it is performed as described above by calculating the standard deviations $\sigma_{Pk}$ of the differences between the measured and best fit times of arrival $t_{hk}$, $t_{BF}$ for each probe $P_k$. Then a further optional step, box 78, is provided in which the best fit times of arrival $t_{BF}$ calculated using all the 'good' time of arrival measurements $t_{hk}$ from the previous iteration of the method 38 and extrapolated to the current iteration. Thus the output of box 58 from the previous iteration is extrapolated to the angle range 360° to 720° and supplied in box 78 for the second and subsequent iterations of the method 38. Then the difference calculated at box 56 via the iteration loop 80 is the difference between the measured times of arrival $t_{hk}$ and the best fit times of arrival $t_{BF}$ extrapolated from the previous revolution. These differences are then passed through the standard deviation calculation, box 64, and compared to the threshold, box 66. The N time of arrival measurements $t_{hk}$ relating to the current revolution for that probe $P_k$ are discarded at box 68 if the standard deviation $\sigma_{Pk}$ of the differences against the extrapolation of the previous revolution best fit exceeds the threshold. For any probe $P_k$ where the standard deviation $\sigma_{Pk}$ of the differences against the extrapolation of the previous revolution best fit does not exceed the threshold, the time of arrival measurements $t_{hk}$ for that revolution of the rotor 2 are optionally used in steps 74, 76 and are used in the calculation at box 58 and for subsequent steps of the method 38.

If either or both of the standard deviation comparison with a threshold (applied once or twice) and the cross-correlation comparison with a threshold are used, the step of calculating the best fit from all the time of arrival measurements $t_{hk}$ (box 58) is amended to use only the times of arrival $t_{hk}$ that have not been discarded at box 68. In most cases no measurements will be discarded for a revolution of the rotor 2 but the optional steps of the method 38 enable 'bad' measurements $t_{hk}$ to be removed from the calculation. Advantageously this improves the accuracy of the seed time $t_s$ calculated by the method 38.

Figure 8:
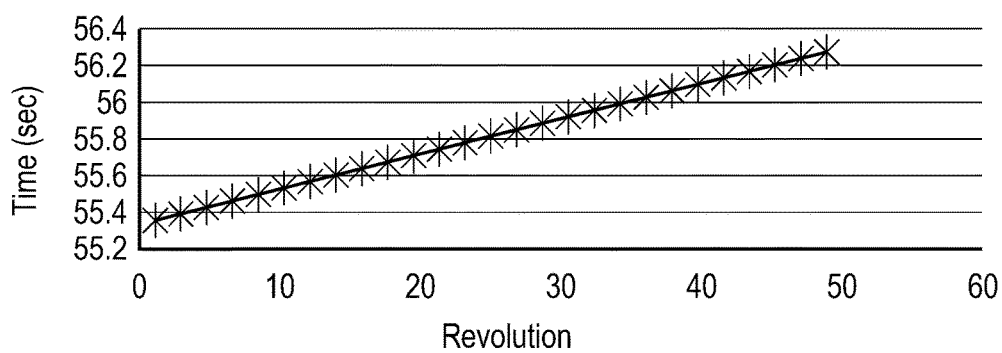
FIG. 8 is a graph showing a time reference derived by the method of the present invention.

FIG. 8 is an exemplary graph of the calculated seed time $t_s$ for iterations of the method 38 corresponding to fifty revolutions of a rotor 2. As is apparent, the individual seed times $t_s$ grow in a stable, linear manner reflecting the fact that the rotor 2 neither accelerated nor decelerated, within an error margin, in the monitored fifty revolutions. The gradient of the line joining the seed time $t_s$ points gives the angular speed of rotation of the rotor 2. The corresponding graph for an accelerating rotor 2 would show a curve upwards through the individual seed times $t_s$ whereas the corresponding graph for a decelerating rotor 2 would show a curve downwards. For each such graph, the rate of change of the gradient of the line joining the seed time $t_s$ points gives the acceleration or deceleration of the rotor 2.

Figure 9:
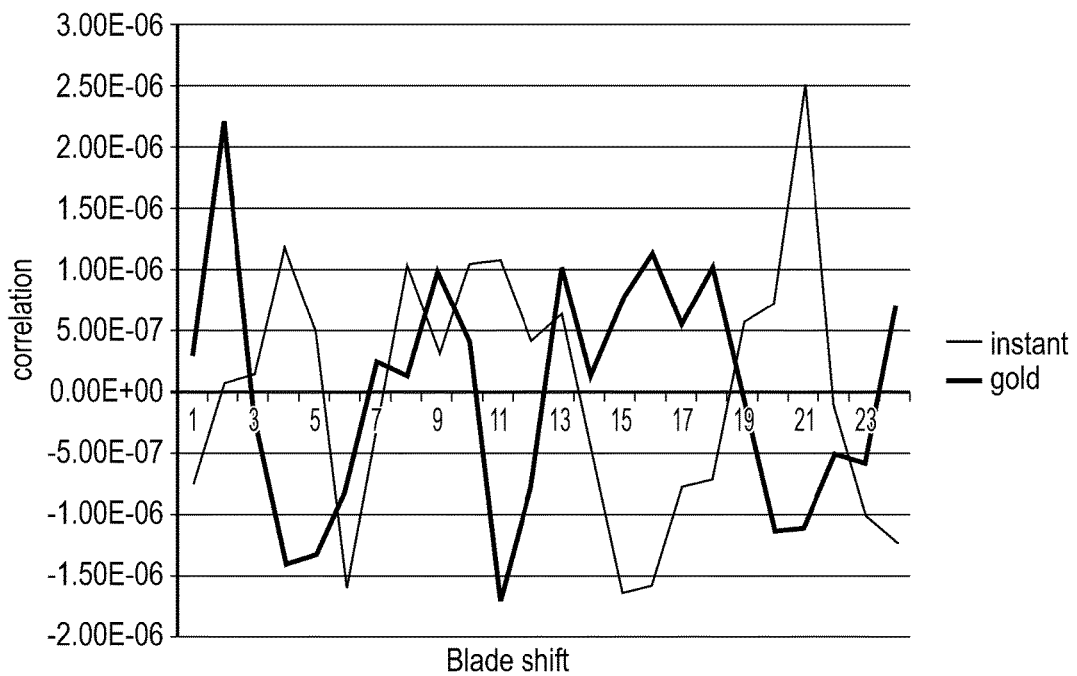
FIG. 9 is a graph showing two stack plots derived from the same probe following a break in measurements.
Figure 10:
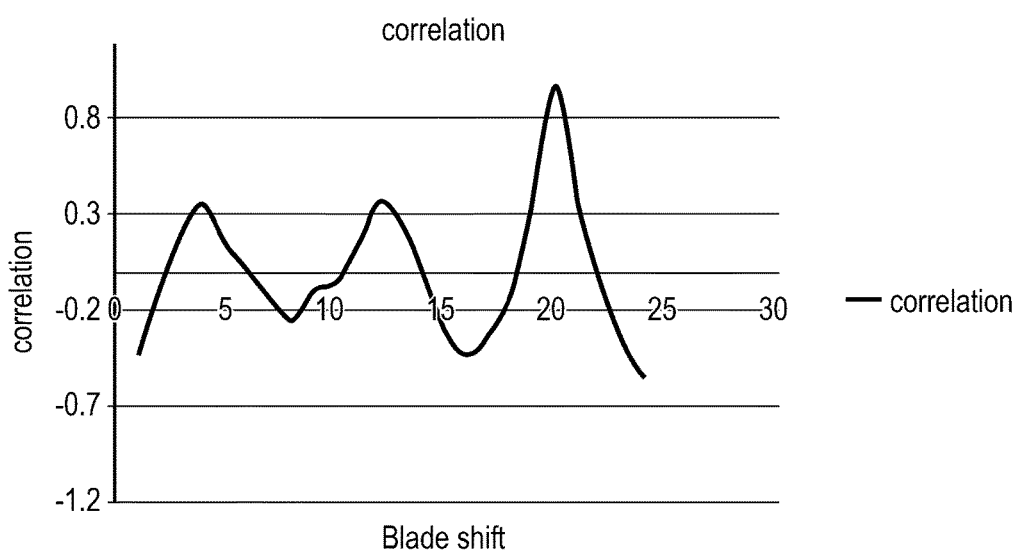
FIG. 10 is a graph showing the correlation of the stack plots in FIG. 9.

For revolutions of the rotor 2 where the time of arrival measurements $t_{hk}$ made at all the probes $P_k$ are discarded at box 68 in FIG. 6 the method is reinitiated. In this case for the next iteration of the method 38 it is necessary to use a stack plot generated in a previous iteration of the method 38 and to iteratively shift the stack plots generated in the current revolution until the cross-correlation between a current stack plot and the previous iteration stack plot exceeds the threshold from box 76 in order to maintain the blade number assignment. This is also necessary where there is a break in the time of arrival measurements $t_{hk}$ for any other reason, for example because the rotor 2 has been stopped and then restarted at a later time. FIG. 9 shows an example of the shift of the stack plot from a probe $P_k$ (relative to itself or another probe $P_k$), labelled "instant", compared to a previous iteration of the method 38, labelled "gold". For example, the "gold" stack plot may have been generated early in the life of the rotor 2. FIG. 10 is a graph of the result of the cross-correlation for each shift of the "instant" stack plot relative to the "gold" stack plot in FIG. 9. As is apparent, the correlation (y-axis) is approximately one when the stack plot is shifted by twenty blade intervals (x-axis).

An advantage of cross-correlating the stack plots from a current revolution of the rotor 2 with those generated in a previous iteration of the method 38 is that vibration analysis and the like may be performed in terms of blade numbers over extended and interruptible periods of time. Thus this benefit of a once per revolution signal produced from an OPR probe can be provided by the method 38 without the need of an OPR probe with its associated weight, size and performance penalties.

The method 38 is preferably encompassed in computer-implemented code and stored on a computer-readable medium. It is thus a computer-implemented method of providing a time reference. The method may be implemented on a basic computer system comprising a processing unit, memory, user interface means such as a keyboard and/or mouse, and display means. The method may be performed 'offline' on data which has been measured and recorded previously. Alternatively it may be performed in 'real-time', that is at the same time that the data is measured. In this case the computer may be coupled to the BTT arrangement. Where the BTT arrangement forms part of a gas turbine engine 10 the computer may be an electronic engine controller or another on-board processor. Where the gas turbine engine 10 powers an aircraft, the computer may be an engine controller, a processor on-board the engine 10 or a processor on-board the aircraft. For example, the method 38 may be used as part of an engine health monitoring system in which real-time blade tip time of arrival measurements $t_{hk}$ are used in the method 38. The engine control may be adjusted based on the output of the method 38.

Although the probes 3 are described as mounted to a casing surrounding the rotor 2 they may be mounted differently. For example, the probes 3 may be mounted to static structure axially forward or rearward of the rotor 2 and directed to see blades 4 or other features as they pass the static probe 3 positions. The probes 3 can therefore detect times of arrival $t_{hk}$ of propeller blades or the like which are not surrounded by a casing meaning that rotor casing is optional.

The probes 3 may be directed radially or may be angled to the radial direction in the axial plane; that is, having no circumferential lean. Although the probes 3 may be angled to also have circumferential lean this component must then be compensated from the time of arrival $t_{hk}$ measurements which adds to the computational burden.

Although a bladed rotor such as a fan 14, compressor rotor stage 16, 18 or turbine rotor stage 22, 24, 26 has been described, aspects are also applicable to a shaft. Such a shaft may have features on its surface from which time of arrival measurements can be made. For example, the shaft surface may comprise grooves, ridges, or lines that are optically distinct from the surrounding surface.

The method 38 has been described with respect to gas turbine engine blade tip timing applications. Such a gas turbine engine 10 may be used for powering an aircraft, in marine or industrial applications. A similar blade tip timing or shaft timing application of the method 38 is found in wind turbines and tidal turbines. However, the method 38 also finds utility in other applications such as shafts and wheels in machine tools, water wheels, power turbines, and turbochargers, in which it is desirable to have one or more stable time reference without having one or multiple OPR probes mounted near the shaft or wheel. It finds particular utility in applications where it is important to minimise size and/or weight.

The method 38 is beneficial for applications where it is necessary to identify the cause of an out of balance error in order to compensate for it, by increasing clearance for example, or to correct it, by adding mass for example. The method 38 is also beneficial for long term health monitoring of rotors, particularly those in inaccessible locations such as land based turbines for oil and gas pumping.

What is claimed is:

1. A method of providing a time reference for a rotor, the rotor comprising N time of arrival features, N being an integer greater than 1; the method comprising steps to:
   a) provide a plurality of time of arrival probes spaced apart circumferentially outside a periphery of the rotor such that during rotation of the rotor each time of arrival feature passes each time of arrival probe;
   b) for each revolution of the rotor, measure a time of arrival of each time of arrival feature at each probe, a first time of arrival measurement measured at a first one of the probes being less than or equal to a first time of arrival measurement measured at any other ones of the probes;
   c) select N time of arrival measurements at each probe, wherein the first time of arrival measurement selected at each probe is greater than or equal to a time reference;
   d) perform a first best fit derivation to derive a best fit of the measured times of arrival measured at all the probes against angular position; and
   e) set the time reference for a next revolution of the rotor equal to the best fit at an end of a current revolution of the rotor,
   the time reference for the next revolution of the rotor being obtained from steps b) through e) without using a Once Per Revolution signal.

2. The method as claimed in claim 1 further comprising, after step c), steps to:
   c1) for times of arrival measured at each probe:
      i) perform a second best fit derivation to derive a best fit of the measured times of arrival against angular position;
      ii) calculate a difference between the measured times of arrival and the best fit times of arrival derived in the second best fit derivation;
      iii) calculate standard deviation of the differences; and
      iv) discard N time of arrival measurements where the standard deviation is greater than a threshold.

3. The method as claimed in claim 2 wherein step c1)ii) comprises subtracting the measured times of arrival from the best fit of the measured times of arrival derived in the second best fit derivation.

4. The method as claimed in claim 2 wherein the threshold used in step c1)iv) is calculated by steps to:
   choose a standard deviation of the differences with an exponent that is equal to the mode of the exponents of all the standard deviations for the current revolution; and
   double it.

5. The method as claimed in claim 2 further comprising a step after step c1)ii) to plot the differences against angular position as a stack plot in time.

6. The method as claimed in claim 5 further comprising a step to identify a missing or additional measured time of arrival measured at a probe.

7. The method as claimed in claim 6 further comprising sub-steps to:
   shift each stack plot by a number of angular intervals equal to a number of angular intervals between the probe and the reference time; and
   perform a cross-correlation of measured times of arrival from pairs of the probes.

8. The method as claimed in claim 7 wherein the step to perform the cross-correlation of measured times of arrival comprises performing the cross-correlation of all the measured times of arrival measured at each of the pair of probes; or performing the cross-correlation of the measured time of arrival of one feature measured at each of the pair of probes.

9. The method as claimed in claim 7 further comprising a step to discard all measured times of arrival measured at a probe if the cross-correlation of the measured times of arrival is less than a predetermined threshold.

10. The method as claimed in claim 1 further comprising a step to calculate a difference between the measured times of arrival measured at one of the probes and the derived best fit of the measured times of arrival, from the first best fit derivation, measured at all the probes for a previous revolution of the rotor.

11. The method as claimed in claim 1 wherein the step of performing the first best fit derivation to derive the best fit of the measured times of arrival comprises plotting the measured times of arrival and fitting a line thereto.

12. A non-transitory computer readable medium, having a computer program recorded thereon, wherein the computer program is adapted to make the computer execute the method according to claim 1.

13. A computer program having instructions adapted to carry out the method according to claim 1 or comprising a non-transitory computer readable medium having a computer program recorded thereon, wherein the computer program is adapted to make the computer execute the method.

14. A rotor arrangement comprising:
   a rotor having time of arrival features;
   a plurality of time of arrival probes spaced apart circumferentially outside the periphery of the rotor; and
   a processor adapted to receive time of arrival measurements from each probe and to calculate the time reference therefrom according to the method of claim 1.

15. The rotor arrangement as claimed in claim 14 wherein the rotor comprises a shaft or a bladed rotor.

16. The rotor arrangement as claimed in claim 15 wherein the probes are unequally spaced circumferentially but are at equal distance from an axis of rotation of the rotor.

17. The rotor arrangement as claimed in claim 14 wherein the time of arrival features comprise any one or more of: rotor blades; grooves; ridges; and lines that are optically distinguished from other parts of the rotor.

18. A gas turbine engine comprising the rotor arrangement as claimed in claim 14.

19. The gas turbine engine as claimed in claim 18 wherein the rotor comprises: a fan rotor; a compressor rotor; a turbine rotor; a shaft; or a propeller rotor.

* * * * *